(12) United States Patent
Mannozzi

(10) Patent No.: US 9,844,500 B2
(45) Date of Patent: Dec. 19, 2017

(54) PROCESS FOR SEMI-PERMANENT STRAIGHTENING OF CURLY, FRIZZY OR WAVY HAIR

(75) Inventor: Alderano Mannozzi, Ascoli Piceno (IT)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 13/580,672

(22) PCT Filed: Feb. 23, 2011

(86) PCT No.: PCT/EP2011/052693
§ 371 (c)(1),
(2), (4) Date: Aug. 23, 2012

(87) PCT Pub. No.: WO2011/104282
PCT Pub. Date: Sep. 1, 2011

(65) Prior Publication Data
US 2012/0312317 A1    Dec. 13, 2012

(30) Foreign Application Priority Data
Feb. 24, 2010 (IT) .............................. MC2010A0028

(51) Int. Cl.
*A61K 8/365*    (2006.01)
*A61Q 5/06*    (2006.01)

(52) U.S. Cl.
CPC ............... *A61K 8/365* (2013.01); *A61Q 5/06* (2013.01)

(58) Field of Classification Search
None
See application file for complete search history.

(56) References Cited

U.S. PATENT DOCUMENTS

| | | | | |
|---|---|---|---|---|
| 2,390,073 A | * | 12/1945 | Calva ....................... | A61K 8/33 132/204 |
| 3,482,581 A | * | 12/1969 | Weigand ................ | A61K 8/345 132/206 |
| 3,910,289 A | | 10/1975 | Wajaroff et al. | |
| 4,591,602 A | | 5/1986 | De Villez | |
| 4,659,566 A | | 4/1987 | Petrow | |
| 6,173,717 B1 | | 1/2001 | Schonert et al. | |
| 6,517,822 B1 | | 2/2003 | Buck | |
| 2003/0143173 A1 | | 7/2003 | Buck | |
| 2005/0048018 A1 | | 3/2005 | Fadeeva et al. | |
| 2006/0074129 A1 | | 4/2006 | Mirabal et al. | |
| 2006/0104928 A1 | | 5/2006 | Furtado | |
| 2006/0260632 A1 | * | 11/2006 | Campain ................ | A61K 8/365 132/204 |
| 2007/0254947 A1 | | 11/2007 | Takiguchi et al. | |
| 2008/0085251 A1 | | 4/2008 | Shibuya et al. | |
| 2008/0223392 A1 | | 9/2008 | Cannell et al. | |
| 2009/0165812 A1 | * | 7/2009 | Resnick et al. ............... | 132/205 |
| 2009/0320869 A1 | | 12/2009 | Fadeeva et al. | |
| 2010/0196303 A1 | * | 8/2010 | Paul ........................ | A61Q 5/06 424/70.11 |
| 2010/0300471 A1 | | 12/2010 | Malle et al. | |
| 2011/0256084 A1 | * | 10/2011 | Dixon et al. ................ | 424/70.2 |
| 2013/0118520 A1 | | 5/2013 | Mannozzi | |
| 2013/0139844 A1 | | 6/2013 | Malle et al. | |
| 2013/0139845 A1 | | 6/2013 | Malle et al. | |
| 2016/0073756 A1 | | 3/2016 | Mannozzi | |

FOREIGN PATENT DOCUMENTS

| | | | | |
|---|---|---|---|---|
| CA | 1258234 A | | 8/1989 | |
| DE | 19505154 | * | 8/1996 | |
| GB | 1 416 564 | | 12/1975 | |
| JP | 2003-137758 A | | 5/2003 | |
| JP | 2007-314528 A | | 12/2007 | |
| JP | 2008-208071 A | | 9/2008 | |
| JP | 2009-537620 A | | 10/2009 | |
| JP | 2013-531046 A | | 8/2013 | |
| SU | 537115 | | 1/1977 | |
| WO | WO-2007/032762 A1 | | 3/2007 | |
| WO | 2007 135299 | | 11/2007 | |
| WO | WO 2012027369 A2 | * | 3/2012 | ............... A61K 8/23 |
| WO | WO-2012/105985 A1 | | 8/2012 | |
| WO | WO 2012/175221 A2 | | 12/2012 | |

OTHER PUBLICATIONS

The website short-hair-style online discussion forum "How about Formaldehyde free Brazilian Keratin Hair Straightener" comments from 2009; http://www.short-hair-style.com/how-about-formaldehyde-free-brazilian-keratin-hair-straightener.html.*
SU 537115 USPTO translation, Jun. 2013.*
CAS Registry entry for "Glyoxylic Acid" accessed 2015.*
Wikipedia entry for "Acid dissociation constant" last modified May 6, 2015; http://en/wikipedia.org/wiki/Acid_dissociation_constant.*
Machine translation DE 19505154, printed 2015.*
"pH of organic acids and salts," last modified Nov. 14, 2015, http://www.aqion.de/site/192.*
International Search Report dated Apr. 11, 2012 in PCT/EP11/052693 Filed Feb. 23, 2011.
Swift, J. Alan, "Fundamentals of Human Hair Science", (Cosmetic Science Monographs, No. 1) Micelle Press, 1997, ISBN: 1-870228-14-6, pp. 4-5.
Dixon and Restnick "Mechanism of straightening hair" with Summary and Appendix, 4 pages, submitted Oct. 23, 2013.
Gadd et al., "An Apparatus to Investigate the Ironing of Chemically Treated Sheepskins", J. Text. Inst., vol. 7, 1979, 318-320.
International Cosmetic Ingredient Dictionary and Handbook, vol. 1, 10th Edition, 2004, p. 551.
International Cosmetic Ingredient Dictionary and Handbook, vol. 2, 10th Edition, 2004, p. 1191.
U.S. Office Action on U.S. Appl. No. 15/425,461 dated Oct. 6, 2017.

* cited by examiner

*Primary Examiner* — David J Blanchard
*Assistant Examiner* — Alissa Prosser
(74) *Attorney, Agent, or Firm* — Foley & Lardner LLP

(57) ABSTRACT

The process of the invention provides for a preventive hair treatment with buffering agent, in particular glyoxylic acid in combination with mechanical straightening with hair straightening iron at temperature of approximately 200° C.+/−50° C.

6 Claims, No Drawings

PROCESS FOR SEMI-PERMANENT STRAIGHTENING OF CURLY, FRIZZY OR WAVY HAIR

The present patent application for industrial invention relates to a process used to semi-permanently straighten curly, frizzy or wavy hair.

1. Glyoxylic acid: it is an alpha-keto acid that can be found in crystalline monohydrate form (CAS No.: 563-96-2) or in aqueous solution (CAS No.: 298-12-4).

Main synonyms: Formylformic acid; alpha-Ketoacetic acid; Glyoxalic acid; Oxalaldehydic acid; Oxoacetic acid; Oxoethanoic acid and others. Its use in the cosmetic sector is considered safe and permitted without any restrictions with indication of the buffering agent function of the pH.

2. Alpha-keto acids: Alpha-keto acids are acids with a carbonylic group in alpha position with respect to the carbon atom of the carboxylic group.

3. Semi-perm: treatment of curly or frizzy hair to straighten it with permanence in such a condition for a number of washings higher than 5.

4. Hair straightening iron: Electrical heating device used in association with a combination of heat and pressure to straighten hair. It is generally composed of two flat heating elements, covered with various materials, between which a lock of hair is pressed at a time. Hair straightening irons are commonly found on the market.

5. Hairdryer: ordinary hair-drying device with heating resistance and fan.

6. Buffering agents: substances dissolved in water to prevent pH changing in the solution for moderate additions of acids or bases (buffering).

Human hair is divided in two types:

a first type of hair, the so-called "Afro" hair (hair with diameter of 70-100 microns), of generally dark color, characterized in that it is more or less curly according to the amount of disulphide groups between the amino acidic chains of keratin (human hair's base protein);

a second type of hair, the so-called "Caucasian" hair (hair with lower diameter than "Afro" hair), either of dark or light color, characterized in that it is less curly than the "Afro" hair, due to the lower amount of disulphide bridges in its keratin structure.

Three types of techniques are currently used to straighten curly or frizzy hair:

a. Treatment with electrical plates basically composed of two hot plates (with temperature higher than 100° C.), between which hair is placed and pressed to obtain desired styling. The result disappears after the first washing with water and shampoo.

b. Low-temperature chemical and mechanical treatment: chemical substances are applied to hair, which is treated at temperatures lower than 100° C., to induce transitory modifications in the aspect of the capillary fiber that disappear after washing hair with water and shampoo.

c. High-temperature chemical and mechanical treatment: chemical substances are applied to hair, which is treated at temperatures higher than 100° C. (same technique as a) above), to induce transitory modifications in the aspect of the capillary fiber that disappear after washing hair with water and shampoo.

Currently, the problem is that, although chemical substances able to straighten human curly, frizzy or wavy hair are known on the market, said substances are impaired by high-toxicity for man and high aggressiveness for hair (i.e.: formaldehyde, sodium hydroxide, sulphur compounds, etc.).

Moreover, it must be said that these processes with chemical substances do not guarantee that treated hair will remain straighten for long after straightening.

The purpose of the present invention is to devise a new chemical-mechanical process (similar to the one illustrated under c) above) to straighten hair semi-permanently (once treated hair will remain straight after a number of washings higher than 5). The innovation consists in the identification of a group of chemical substances that, when combined with a high-temperature mechanical treatment, unlike the state of the art, allow for obtaining straight, soft, shiny and volumeless hair from curly and frizzy hair, said characteristics being maintained also after repeated washings with water and shampoo.

A further purpose of the invention is to devise a process with the aforesaid features, which uses buffering agents in very low percentage, and in any case lower than the values used in the known process, thus reducing the stress for treated hair.

These purposes are achieved according to the invention, with the characteristics that are listed in the attached independent claim 1.

Advantageous realizations appear from the dependent claims.

The process of the invention provides for the combined action of mechanical pressing with hot plates at a temperature of approximately 200° C. (+/−50° C.) with preventive hair treatment with a solution containing a buffering agent.

More precisely, the process provides for:

a) Application on hair of a solution containing a buffering acid agent from the alpha-ketoacids family;

b) Permanence of said substance in contact with hair for 15 to 120 minutes;

c) Hair drying, d) Straightening of hair with hair straightening iron at temperature of approximately 200+/−50 C.°;

In particular, the process of the invention has proved to induce semi-permanent modifications in the hair structure, which will remain such after repeatedly washing hair in normal conditions of use.

Studies carried out on the chemical substances that are already used in the cosmetic sector and tests carried out on hair have resulted in the selection of some substances, which are already known for their pH buffering properties, which, when used in combination with mechanical straightening, allow for semi-permanently eliminating the typical curves that characterize curly, frizzy or wavy hair.

In particular, the reduction or elimination of "curves" in hair is expressed as easier-to-comb hair and lower global volume of the capillary fiber due to the elimination of said curves (and, consequently, a reduction of the volume occupied by hair in the space).

Table 1 contains a list of all buffering agents that are known today and are included in the European Inventory of ingredients used in cosmetic products, attached to Decision no. 1996/335/CE dated Aug. 5, 1996, and following amendments and integrations.

The process according to the invention advantageously uses glyoxylic acid in aqueous solution, which has demonstrated to give appreciable results compared to the other buffering agents contained in the aforementioned list.

Moreover, also the substances listed in Table 2 have been tested, mixed with one of the buffering agents, which are contained in the list attached to the Decision no. 1996/335/CE dated Aug. 5, 1996 and following amendments and integrations.

Further characteristics of the invention will become apparent from the detailed description below.

Amongst the substances contained in the European list of ingredients used in cosmetic products and having a buffering function that have been experimented within the process of the invention, glyoxylic acid has given the best results.

Tests consisted in dissolving 10 grams of glyoxylic acid in 100 milliliters of water.

More precisely, with ponderal ratio comprised between 5 and 25%.

In one embodiment, the process further comprises pre-washing the hair with a basic shampoo having a pH of from 7.5 to 9.5 prior to applying the solution, and rinsing said hair after said straightening. In particular, hair was washed with basic pH (7.5-8.5) shampoo, then said glyoxylic acid solution was applied (application can be made with hard bristle brush, spray or in any other way).

However, it must be noted that said pre-washing with said basic pH shampoo did not prove to be fundamental for semi-permanent hair straightening.

Hair was left in contact with the substance for 60 minute time (+/−30 minutes) and then dried with the hairdryer.

Once dried, hair was straightened with hair straightening iron heated at average temperature of approximately 200 C.°, +/−50 C.°. It must be noted that the materials of the iron plates do not affect the process of the invention.

In one embodiment, the process further comprises washing the hair with an acidic shampoo having a pH of approximately from 4.5 to 5.5 after the straightening. Finally, hair was rinsed again with water or washed again with shampoo and dried.

At the end of treatment, hair was shiny, straight, volumeless, soft to touch, and especially pleasant.

The tests demonstrated the efficacy of the invention both on natural and chemically dyed or bleached hair.

It was experimentally proved that the efficacy of treatment is maintained over time for at least six washings, rinsings and dryings in normal use conditions of hair shampoo (as confirmed by the values contained in the tables attached to the end of this description: Tables 1-A to 1-D).

Further tests were carried out by adding one of the substances listed in table 2 to the glyoxylic acid solution.

Each substance was tested in a mixture with such glyoxylic acid solution by adding 10 grams of one of the substances listed in table 2 to 100 milliliters of said solution.

Following is a typical composition of said mixture:

EXAMPLE 1

| Water | 100 milliliters |
|---|---|
| Glyoxylic acid | 10 grams |
| Potassium iodide | 10 grams |

EXAMPLE 2

| Water | 100 milliliters |
|---|---|
| Glyoxylic acid | 10 grams |
| Dihydroxyacetone | 10 grams |

EXAMPLE 3

| Water | 100 milliliters |
|---|---|
| Glyoxylic acid | 10 grams |

-continued

| Ozonized jojoba oil | 10 grams |
|---|---|
| Inert emulsifying agent (glycerol) | 10 grams |

EXAMPLE 4

| Water | 100 milliliters |
|---|---|
| Glyoxylic acid | 10 grams |
| 2,4 hexadienal | 10 grams |

In example 3 an emulsifying agent (glycerol), which is inert for hair straightening, was added to the solution to facilitate ozonized jojoba oil dispersion in aqueous solution.

The mixture obtained in example 3 is an oily mixture due to the use of jojoba oil.

Also at the end of treatments carried out with the mixtures illustrated in examples 1, 2, 3 and 4, hair was shiny, straight, volumeless, soft to touch and especially pleasant; moreover, hair straightening was tested in terms of time permanence.

Further tests were carried out to see whether the effect obtained with aqueous solutions could be repeated also when said substances were part of a commercial cosmetic formulation (i.e. mixed with other substances that are normally used in the cosmetic sector).

An additional test was carried out by adding glyoxylic acid (and its mixtures with potassium iodide, dihydroxyacetone, ozonized jojoba oil and 2,4 hexadienal illustrated in examples 1, 2, 3 and 4) with hair treatment cosmetics found on the market.

In particular, a hair straightening test was carried out using the formulation of a cosmetic product by INOAR Cosmeticos Ltda of San Paulo, Brazil, known as "Tratamento capillar marroquino". The product was deprived of its active ingredient for hair straightening.

10 grams of glyoxylic acid were added to 100 milliliters of said cosmetic and, after carrying out the same hair treatment operations illustrated in the foregoing pages, the results were identical to the ones achieved using the same percentage ratio of glyoxylic acid in water.

At the end of treatment, hair was permanently shiny, straight, volumeless, and soft to touch, and with an especially pleasant look.

Similar results were obtained from four tests made with four mixtures identical to the ones of examples 1, 2, 3, and 4, using 100 milliliters of cosmetic product instead of 100 milliliters of acidulated water.

Hair was straight, volumeless, soft to touch and especially shiny when exposed to sunlight or artificial light.

Experimentally, it was finally ascertained that the best range is comprised between 5% and 25% of the substances listed in table 2, so that the weight percentage of each of them is included between 5% and 25%, with completion to 100 made of inert substances with respect to straightening of curly, frizzy or wavy hair.

It must be noted that tests have demonstrated that the hair straightening effect, with consequent volume reduction, is not appreciated when heating hair at temperatures of approximately 50-60° C. with an ordinary hairdryer, whereas it is clearly visible until the first rinsing and/or shampooing in case of treatment for a few seconds at temperatures of approximately 200+/−50 C.°.

Said tests have also demonstrated that the higher the contact time of the invention and its mixtures with the capillary fiber, the higher the hair straightening effect will be.

TABLE 1-A

GLYOXYLIC ACID
"AFRO" NATURAL CURLY HAIR IRON at 200° C.
STRAIGHTENING EFFECT ASSESSMENT (curve reduction)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| WATER 100 ml | 5.5 | 6.0 | (−) | (−) | (−) | (−) | (−) | (−) |
| WATER 95 ml + GLYOXYLIC ACID 5 g | 2.1 | 2.1 | (+++) | (++) | (+) | (+) | (+) | (+/−) |
| WATER 90 ml + GLYOXYLIC ACID 10 g | 2.0 | 2.0 | (++++) | (+++) | (++) | (++) | (++) | (+) |
| WATER 85 ml + GLYOXYLIC ACID 15 g | 1.8 | 1.8 | (+++) | (+++) | (++) | (++) | (++) | (+) |
| WATER 80 ml + GLYOXYLIC ACID 20 g | 1.6 | 1.6 | (++) | (++) | (+) | (+) | (+) | (+/−) |
| WATER 80 ml + GLYOXYLIC ACID 25 g | 1.5 | 1.5 | (++) | (++) | (+) | (+) | (+) | (+/−) |
| WATER 100 ml + GLYOXYLIC ACID 10 g + Potassium Iodide 10 g | 2.0 | 2.0 | (++) | (++) | (+) | (+) | (+/−) | (+/−) |
| WATER 100 ml + GLYOXYLIC ACID 10 g + Dihydroxyacetone 10 g | 2.0 | 2.0 | (+++) | (+++) | (+) | (++) | (+) | (+/−) |
| WATER 100 ml + GLYOXYLIC ACID 10 g + Ozonized Jojoba Oil 10 g + glycerol 10 g | 2.0 | 2.0 | (++++) | (+++) | (++) | (+) | (+) | (+/−) |
| WATER 100 ml + GLYOXYLIC ACID 10 g + 2,4 Hexadienal 10 g | 2.0 | 2.0 | (+++) | (++) | (+) | (+) | (+/−) | (+/−) |
| GLYOXILIC ACID 10 g + cosmetic base 100 ml | 2.1 | 2.1 | (++++) | (+++) | (++) | (++) | (++) | (+) |
| GLYOXYLIC ACID 10 g + Potassium Iodide 10 gr + cosmetic base 100 ml | 2.0 | 2.1 | (++) | (++) | (+) | (+) | (+/−) | (+/−) |
| GLYOXILIC ACID 10 g + Dihydroxyacetone 10 g + cosmetic base 100 ml | 1.9 | 1.9 | (+++) | (+++) | (+) | (++) | (+) | (+/−) |
| GLYOXYLIC ACID 10 g + Ozonized Jojoba Oil 10 g + cosmetic base 100 ml | 2.1 | 1.9 | (++++) | (+++) | (++) | (+) | (+) | (+/−) |
| GLYOXYLIC ACID 10 g + Dihydroxyacetone 10 g + cosmetic base 100 ml | 2.0 | 1.9 | (+++) | (++) | (+) | (+) | (+/−) | (+/−) |
| MEASURED PARAMETER | | | No effect | Reduction lower than 25% | Reduction between 26 and 50% | Reduction between 51 and 75% | Reduction between 76 and 90% | 100% reduction |
| % Reduction of curves in 20 cm of hair (residual curves/total curves *100) | | | − | +/− | + | ++ | +++ | ++++ |

TABLE 1-B

GLYOXYLIC ACID
"European" NATURAL CURLY HAIR IRON at 200° C.
STRAIGHTENING EFFECT ASSESSMENT (curve reduction)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| WATER 100 ml | 5.5 | 6.0 | (−) | (−) | (−) | (−) | (−) | (−) |
| WATER 95 ml + GLYOXYLIC ACID 5 g | 2.1 | 2.1 | (+++) | (++) | (++) | (+) | (+) | (+/−) |
| WATER 90 ml + GLYOXYLIC ACID 10 g | 2.0 | 2.0 | (++++) | (+++) | (+++) | (++) | (++) | (++) |
| WATER 85 ml + | 1.8 | 1.8 | (+++) | (+++) | (+++) | (+++) | (++) | (++) |

TABLE 1-B-continued

GLYOXYLIC ACID
"European" NATURAL CURLY HAIR IRON at 200° C.
STRAIGHTENING EFFECT ASSESSMENT (curve reduction)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| GLYOXYLIC ACID 15 g WATER 80 ml + | 1.6 | 1.6 | (++) | (++) | (+) | (+) | (+) | (+/−) |
| GLYOXYLIC ACID 20 g WATER 80 ml + | 1.5 | 1.5 | (++) | (++) | (+) | (+) | (+) | (+/−) |
| GLYOXYLIC ACID 25 g WATER 100 ml + | 2.0 | 2.0 | (++) | (++) | (+) | (+) | (+/−) | (+/−) |
| GLYOXYLIC ACID 10 g + Potassium Iodide 10 g WATER 100 ml + | 2.0 | 2.0 | (+++) | (+++) | (++) | (++) | (+) | (+) |
| GLYOXYLIC ACID 10 g + Dihydroxyacetone 10 g WATER 100 ml + | 2.0 | 2.0 | (++++) | (+++) | (++) | (+) | (+) | (+) |
| GLYOXYLIC ACID 10 g + Ozonized Jojoba Oil 10 g + glycerol 10 g WATER 100 ml + | 2.0 | 2.0 | (+++) | (++) | (+) | (+) | (+) | (+) |
| GLYOXYLIC ACID 10 g + 2,4 Hexadienal 10 g | | | | | | | | |
| GLYOXYLIC ACID 10 g + cosmetic base 100 ml | 2.1 | 2.1 | (++++) | (+++) | (++) | (++) | (++) | (+) |
| GLYOXYLIC ACID 10 g + Potassium Iodide 10 gr + cosmetic base 100 ml | 2.0 | 2.1 | (+++) | (++) | (++) | (++) | (+) | (+) |
| GLYOXYLIC ACID 10 g + Dihydroxyacetone 10 g + cosmetic base 100 ml | 1.9 | 1.9 | (+++) | (+++) | (++) | (++) | (+) | (+) |
| GLYOXYLIC ACID 10 g + Ozonized Jojoba Oil 10 g + cosmetic base 100 ml | 2.1 | 1.9 | (++++) | (+++) | (++) | (++) | (+) | (+) |
| GLYOXYLIC ACID 10 g + Dihydroxyacetone 10 g + cosmetic base 100 ml | 2.0 | 1.9 | (+++) | (++) | (++) | (++) | (+) | (+) |
| MEASURED PARAMETER | | | No effect | Reduction lower than 25% | Reduction between 26 and 50% | Reduction between 51 and 75% | Reduction between 76 and 90% | 100% reduction |
| % Reduction of curves in 20 cm of hair (residual curves/total curves *100) | | | − | +/− | + | ++ | +++ | ++++ |

TABLE 1-C

GLYOXYLIC ACID
"AFRO" NATURAL CURLY HAIR IRON at 200° C.
VOLUME REDUCTION ASSESSMENT (reduction of hair spatial volume)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| WATER 100 ml | 5.5 | 6.0 | (−) | (−) | (−) | (−) | (−) | (−) |
| WATER 95 ml + GLYOXYLIC ACID 5 g | 2.1 | 2.1 | (++) | (++) | (+) | (+) | (+/−) | (+/−) |
| WATER 90 ml + GLYOXYLIC ACID 10 g | 2.0 | 2.0 | (++++) | (+++) | (++) | (++) | (++) | (+) |
| WATER 85 ml + GLYOXYLIC ACID 15 g | 1.8 | 1.8 | (+++) | (+++) | (++) | (++) | (++) | (+) |
| WATER 80 ml + GLYOXYLIC ACID 20 g | 1.6 | 1.6 | (++) | (++) | (+) | (+) | (+) | (+) |
| WATER 80 ml + GLYOXYLIC ACID 25 g | 1.5 | 1.5 | (++) | (++) | (+) | (+) | (+) | (+) |
| WATER 100 ml + | 2.0 | 2.0 | (++) | (++) | (+) | (+) | (+) | (+) |

TABLE 1-C-continued

GLYOXYLIC ACID
"AFRO" NATURAL CURLY HAIR IRON at 200° C.
VOLUME REDUCTION ASSESSMENT (reduction of hair spatial volume)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| GLYOXYLIC ACID 10 g + Potassium Iodide 10 g WATER 100 ml + | 2.0 | 2.0 | (+++) | (+++) | (+) | (++) | (+) | (+) |
| GLYOXYLIC ACID 10 g + Dihydroxyacetone 10 g WATER 100 ml + | 2.0 | 2.0 | (++++) | (+++) | (++) | (++) | (+) | (+) |
| GLYOXYLIC ACID 10 g + Ozonized Jojoba Oil 10 g + glycerol 10 g WATER 100 ml + | 2.0 | 2.0 | (+++) | (++) | (++) | (+) | (+) | (+) |
| GLYOXYLIC ACID 10 g + 2,4 Hexadienal 10 g | 2.1 | 2.1 | (++++) | (+++) | (++) | (++) | (++) | (+) |
| GLYOXYLIC ACID 10 g + cosmetic base 100 ml | 2.0 | 2.1 | (++) | (++) | (+) | (+) | (+/−) | (+) |
| GLYOXYLIC ACID 10 g + Potassium Iodide 10 gr + cosmetic base 100 ml | 1.9 | 1.9 | (+++) | (+++) | (+) | (++) | (+) | (+) |
| GLYOXYLIC ACID 10 g + Dihydroxyacetone 10 g + cosmetic base 100 ml | 2.1 | 1.9 | (++++) | (+++) | (++) | (+) | (+) | (+) |
| GLYOXYLIC ACID 10 g + Ozonized Jojoba Oil 10 g + cosmetic base 100 ml | 2.0 | 1.9 | (+++) | (++) | (++) | (+) | (+) | (+) |
| GLYOXYLIC ACID 10 g + Dihydroxyacetone 10 g + cosmetic base 100 ml | | | | | | | | |
| MEASURED PARAMETER | | | No effect | Reduction lower than 25% | Reduction between 26 and 50% | Reduction between 51 and 75% | Reduction between 76 and 90% | 100% reduction |
| % Reduction of hair volume (circumference of lock with 1.0 g weight measured at half length) (final diameter/initial diameter *100) | | | − | +/− | + | ++ | +++ | ++++ |

TABLE 1-D

GLYOXYLIC ACID
"European" NATURAL CURLY HAIR IRON at 200° C.
VOLUME REDUCTION ASSESSMENT (reduction of hair spatial volume)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| WATER 100 ml | 5.5 | 6.0 | (−) | (−) | (−) | (−) | (−) | (−) |
| WATER 95 ml + GLYOXYLIC ACID 5 g | 2.1 | 2.1 | (+++) | (++) | (++) | (++) | (+) | (+/−) |
| WATER 90 ml + GLYOXYLIC ACID 10 g | 2.0 | 2.0 | (++++) | (+++) | (+++) | (++) | (++) | (++) |
| WATER 85 ml + GLYOXYLIC ACID 15 g | 1.8 | 1.8 | (+++) | (+++) | (+++) | (+++) | (++) | (++) |
| WATER 80 ml + GLYOXYLIC ACID 20 g | 1.6 | 1.6 | (++) | (++) | (+) | (+) | (+) | (+) |
| WATER 80 ml + GLYOXYLIC ACID 25 g | 1.5 | 1.5 | (++) | (++) | (++) | (++) | (+) | (+) |
| WATER 100 ml + GLYOXYLIC ACID 10 g + Potassium Iodide 10 g | 2.0 | 2.0 | (++) | (++) | (++) | (+) | (+) | (+) |
| WATER 100 ml + GLYOXYLIC ACID 10 g + Dihydroxyacetone 10 g | 2.0 | 2.0 | (+++) | (+++) | (++) | (++) | (+) | (+) |

TABLE 1-D-continued

GLYOXYLIC ACID
"European" NATURAL CURLY HAIR IRON at 200° C.
VOLUME REDUCTION ASSESSMENT (reduction of hair spatial volume)

| TESTED MIX | pH of initial mix | pH after contact with hair washed with basic shampoo | after no. 1 washing and drying | after no. 2 washings and dryings | after no. 3 washings and dryings | after no. 4 washings and dryings | after no. 5 washings and dryings | after no. 6 washings and dryings |
|---|---|---|---|---|---|---|---|---|
| WATER 100 ml + GLYOXYLIC ACID 10 g + Ozonized Jojoba Oil 10 g + glycerol 10 g | 2.0 | 2.0 | (++++) | (+++) | (++) | (++) | (+) | (+) |
| WATER 100 ml + GLYOXYLIC ACID 10 g + 2,4 Hexadienal 10 g | 2.0 | 2.0 | (+++) | (++) | (+) | (+) | (+) | (+) |
| GLYOXYLIC ACID 10 g + cosmetic base 100 ml | 2.1 | 2.1 | (++++) | (+++) | (++) | (++) | (++) | (+) |
| GLYOXYLIC ACID 10 g + Potassium Iodide 10 gr + cosmetic base 100 ml | 2.0 | 2.1 | (+++) | (++) | (++) | (++) | (+) | (+) |
| GLYOXYLIC ACID 10 g + Dihydroxyacetone 10 g + cosmetic base 100 ml | 1.9 | 1.9 | (+++) | (+++) | (++) | (++) | (+) | (+) |
| GLYOXYLIC ACID 10 g + Ozonized Jojoba Oil 10 g + cosmetic base 100 ml | 2.1 | 1.9 | (++++) | (+++) | (++) | (++) | (+) | (+) |
| GLYOXYLIC ACID 10 g + Dihydroxyacetone 10 g + cosmetic base 100 ml | 2.0 | 1.9 | (+++) | (++) | (++) | (++) | (+) | (+) |
| MEASURED PARAMETER | | | No effect | Reduction lower than 25% | Reduction between 26 and 50% | Reduction between 51 and 75% | Reduction between 76 and 90% | 100% reduction |
| % Reduction of hair volume (circumference of lock with 1.0 g weight measured at half length) (final diameter/initial diameter *100) | | | − | +/− | + | ++ | +++ | ++++ |

| TABLE 1 | | | TABLE 1-continued | |
|---|---|---|---|---|
| N. | Name INCI | | N. | Name INCI |
| 1 | 1,6-HEXANEDIAMINE | | 33 | BISMUTH CITRATE |
| 2 | 2-AMINOBUTANOL | | 34 | BORIC ACID |
| 4 | ACETYL MANDELIC ACID | | 35 | CALCIUM CARBONATE |
| 5 | ADIPIC ACID | | 36 | CALCIUM CITRATE |
| 6 | ALUMINUM GLYCINATE | | 37 | CALCIUM DIHYDROGEN PHOSPHATE |
| 7 | ALUMINUM LACTATE | | 38 | CALCIUM HYDROXIDE |
| 8 | ALUMINUM TRIFORMATE | | 39 | CALCIUM LACTATE |
| 9 | AMINOETHYL PROPANEDIOL | | 40 | CALCIUM OXIDE |
| 10 | AMINOMETHYL PROPANEDIOL | | 41 | CALCIUM PHOSPHATE |
| 11 | AMINOMETHYL PROPANOL | | 42 | CITRIC ACID |
| 12 | AMINOPROPANEDIOL | | 43 | CLAY MINERALS |
| 13 | AMMONIA | | 44 | CYCLOHEXYLAMINE |
| 14 | AMMONIUM ACETATE | | 45 | DECAPEPTIDE-7 |
| 15 | AMMONIUM BICARBONATE | | 46 | DIAMMONIUM CITRATE |
| 16 | AMMONIUM CARBAMATE | | 47 | DIAMMONIUM PHOSPHATE |
| 17 | AMMONIUM CARBONATE | | 48 | DIBUTYL ETHANOLAMINE |
| 18 | AMMONIUM CHLORIDE | | 49 | DIETHYL ETHANOLAMINE |
| 19 | AMMONIUM GLYCOLATE | | 50 | DIMETHYL ISOPROPANOLAMINE |
| 20 | AMMONIUM HYDROXIDE | | 51 | DIMETHYL MEA |
| 21 | AMMONIUM LACTATE | | 52 | DIOLEOYL EDETOLMONIUM METHOSULFATE |
| 22 | AMMONIUM MOLYBDATE | | 53 | DIOLEYL PHOSPHATE |
| 23 | AMMONIUM NITRATE | | 54 | DIPOTASSIUM PHOSPHATE |
| 24 | AMMONIUM PHOSPHATE | | 55 | DIPROPYLENETRIAMINE |
| 25 | AMMONIUM THIOCYANATE | | 56 | DISODIUM FUMARATE |
| 26 | AMMONIUM VANADATE | | 57 | DISODIUM PHOSPHATE |
| 27 | ASCORBIC ACID | | 58 | DISODIUM PYROPHOSPHATE |
| 28 | AZELAIC ACID | | 59 | DISODIUM TARTRATE |
| 29 | BABASSU ACID | | 60 | ETHANOLAMINE |
| 30 | BAKUHAN | | 61 | ETHANOLAMINE HCl |
| 31 | BENZILIC ACID | | 62 | ETHYL ETHANOLAMINE |
| 32 | BIS-HYDROXYETHYL TROMETHAMINE | | 63 | FUMARIC ACID |

TABLE 1-continued

| N. | Name INCI |
|---|---|
| 64 | GALACTURONIC ACID |
| 65 | GLUCOHEPTONIC ACID |
| 66 | GLUCONIC ACID |
| 67 | GLUCURONIC ACID |
| 68 | GLUTARIC ACID |
| 69 | GLYCINE |
| 70 | GLYCOLIC ACID |
| 71 | GLYOXYLIC ACID |
| 72 | GUANIDINE CARBONATE |
| 73 | GUANIDINE HCl |
| 74 | HYDROBROMIC ACID |
| 75 | HYDROCHLORIC ACID |
| 76 | HYDROXYETHYLPIPERAZINE ETHANE SULFONIC ACID |
| 77 | IMIDAZOLE |
| 78 | ISOBUTYRIC ACID |
| 79 | ISOPROPANOLAMINE |
| 80 | ISOPROPYLAMINE |
| 81 | LACTIC ACID |
| 82 | LACTOBIONIC ACID |
| 83 | LAURYL p-CRESOL KETOXIME |
| 84 | LITHIUM HYDROXIDE |
| 85 | MAGNESIUM ACETATE |
| 86 | MAGNESIUM CARBONATE HYDROXIDE |
| 87 | MAGNESIUM HYDROXIDE |
| 88 | MAGNESIUM LACTATE |
| 89 | MAGNESIUM OXIDE |
| 90 | MALEIC ACID |
| 91 | MALIC ACID |
| 92 | MALONIC ACID |
| 93 | MALTOBIONIC ACID |
| 94 | MEA-BORATE |
| 95 | METAPHOSPHORIC ACID |
| 96 | METHOXY PEG-114/POLYEPSILON CAPROLACTONE |
| 97 | METHYLETHANOLAMINE |
| 98 | MONOSODIUM CITRATE |
| 99 | PENTAPOTASSIUM TRIPHOSPHATE |
| 100 | PENTASODIUM TRIPHOSPHATE |
| 101 | PHENYL MERCURIC BORATE |
| 102 | PHOSPHONOBUTANETRICARBOXYLIC ACID |
| 103 | PHOSPHORIC ACID |
| 104 | PHOSPHORUS PENTOXIDE |
| 105 | POTASSIUM BICARBONATE |
| 106 | POTASSIUM BIPHTHALATE |
| 107 | POTASSIUM BORATE |
| 108 | POTASSIUM CARBONATE |
| 109 | POTASSIUM CITRATE |
| 110 | POTASSIUM HYDROXIDE |
| 111 | POTASSIUM LACTATE |
| 112 | POTASSIUM MAGNESIUM ASPARTATE |
| 113 | POTASSIUM OXIDE |
| 114 | POTASSIUM PHOSPHATE |
| 115 | POTASSIUM SODIUM TARTRATE |
| 116 | POTASSIUM TARTRATE |
| 117 | PROPANE TRICARBOXYLIC ACID |
| 118 | QUINIC ACID |
| 119 | RIBONIC ACID |
| 120 | SEBACIC ACID |
| 121 | SODIUM ACETATE |
| 122 | SODIUM ALUMINATE |
| 123 | SODIUM ALUMINUM LACTATE |
| 124 | SODIUM ARACHIDATE |
| 125 | SODIUM ASPARTATE |
| 126 | SODIUM BICARBONATE |
| 127 | SODIUM BISULFATE |
| 128 | SODIUM BORATE |
| 129 | SODIUM BUTOXYETHOXY ACETATE |
| 130 | SODIUM CARBONATE |
| 131 | SODIUM CITRATE |
| 132 | SODIUM FORMATE |
| 133 | SODIUM FUMARATE |
| 134 | SODIUM GLYCOLATE |
| 135 | SODIUM HUMATE |
| 136 | SODIUM HYDROXIDE |
| 137 | SODIUM LACTATE |
| 138 | SODIUM METAPHOSPHATE |
| 139 | SODIUM METASILICATE |
| 140 | SODIUM OXIDE |
| 141 | SODIUM PHOSPHATE |

TABLE 1-continued

| N. | Name INCI |
|---|---|
| 142 | SODIUM SESQUICARBONATE |
| 143 | SODIUM SILICATE |
| 144 | SODIUM SUCCINATE |
| 145 | SODIUM TRIMETAPHOSPHATE |
| 146 | STRONTIUM HYDROXIDE |
| 147 | SUCCINIC ACID |
| 148 | SULFURIC ACID |
| 149 | TARTARIC ACID |
| 150 | TAURINE |
| 151 | TEA-DIRICINOLEATE/IPDI COPOLYMER |
| 152 | TEA-HYDROIODIDE |
| 153 | TEA-SULFATE |
| 154 | TETRAHYDROXYETHYL ETHYLENEDIAMINE |
| 155 | TETRAPOTASSIUM PYROPHOSPHATE |
| 156 | TETRASODIUM PYROPHOSPHATE |
| 157 | TRIETHANOLAMINE |
| 158 | TRIISOPROPANOLAMINE |
| 159 | TRISODIUM PHOSPHATE |
| 160 | TRISODIUM SULFOSUCCINATE |
| 161 | TRITICUM VULGARE PROTEIN |
| 162 | TRITICUM VULGARE SEED EXTRACT |
| 163 | TROMETHAMINE |
| 164 | UREA |
| 165 | URIC ACID |
| 166 | ZINC CARBONATE HYDROXIDE |
| 167 | ZINC GLYCINATE |
| 168 | ZINC HEXAMETAPHOSPHATE |
| 169 | ZINC MAGNESIUM ASPARTATE |

TABLE 2 potassium iodide CAS n. 7681-11-0 (Used as antimicrobial)
dihydroxyacetone CAS n. 96-26-4 (Used as tanning)
Ozonized Jojoba oil (No n. CAS) (Used as emollient)
2,4 Hexadienal CAS n. 142-83-6 (Used as perfuming)

The invention claimed is:

1. A process for semi-permanent hair straightening, comprising
    a) applying a solution comprising glyoxylic acid at a pH of 1.5-2.1, wherein the hair is prewashed prior to said applying;
    b) keeping the solution in contact with hair for 15 to 120 minutes, wherein said keeping has an average duration of 60 minutes;
    c) drying the hair, and
    d) straightening the hair with a hair straightening iron at temperature of approximately 200+/−50° C.
    wherein the hair is human hair and said glyoxylic acid is dissolved in aqueous solution in ponderal ratio between 5% and 10% in weight.

2. The process as claimed in claim 1, further comprising prewashing the hair with a basic shampoo having a pH of from 7.5 to 9.5 prior to said applying; and rinsing said hair after said straightening.

3. The process as claimed in claim 1, further comprising washing the hair with an acidic shampoo having a pH of approximately from 4.5 to 5.5 after said straightening.

4. The process as claimed in claim 1, wherein said glyoxylic acid is mixed with at least one member selected from the group consisting of potassium iodide, dihydroxyacetone, ozonized jojoba oil, and 2,4-hexadienal.

5. The process as claimed in claim 1, wherein said glyoxylic acid is mixed with at least one additive selected from the group consisting of potassium iodide, dihydroxyacetone, ozonized jojoba oil, and 2,4-hexadienal, wherein said at least one additive is present in an amount of 5% to 25% in weight of the solution, and the solution comprises, in an amount to form 100% in weight of the solution, an inert cosmetic substance operable for the straightening of curly, frizzy, or wavy hair.

6. The process as claimed in claim 1, further comprising washing the hair with a shampoo after said straightening.

\* \* \* \* \*